US005989588A

United States Patent [19]
Korn et al.

[11] Patent Number: 5,989,588
[45] Date of Patent: Nov. 23, 1999

[54] METHODS AND COMPOSITIONS FOR PREVENTING AND TREATING HEARTBURN

[75] Inventors: Scott H. Korn, Richboro; Gerard P. McNally, Strafford; Joseph R. Luber, Quakertown; Tom S. Ells, Fort Washington, all of Pa.

[73] Assignees: Merck & Co., Inc., Rahway, N.Y.; McNeil-PPC, Inc., Skillman, N.J.

[21] Appl. No.: 08/940,643

[22] Filed: Sep. 30, 1997

Related U.S. Application Data

[60] Provisional application No. 60/027,659, Oct. 4, 1996.

[51] Int. Cl.[6] ............................. A61K 9/20; A61K 9/48
[52] U.S. Cl. ........................................ 424/465; 424/451
[58] Field of Search ................... 424/401, 464, 424/465, 451

[56] References Cited

U.S. PATENT DOCUMENTS

| | | | |
|---|---|---|---|
| 4,283,408 | 8/1981 | Hirata et al. | 424/270 |
| 5,229,137 | 7/1993 | Wolfe et al. | 424/687 |
| 5,629,026 | 5/1997 | Davis et al. | 424/686 |
| 5,667,794 | 9/1997 | Simon et al. | 424/401 |

FOREIGN PATENT DOCUMENTS

| | | |
|---|---|---|
| 0 138 540 | 4/1985 | European Pat. Off. . |
| 0 233 853 | 8/1987 | European Pat. Off. . |
| 0 290 229 | 11/1988 | European Pat. Off. . |
| 0 294 933 | 12/1988 | European Pat. Off. . |
| 0 492 247 A1 | 7/1992 | European Pat. Off. . |
| 0 600 725 A1 | 6/1994 | European Pat. Off. . |
| WO 92/00102 | 1/1992 | WIPO . |
| WO 93/12779 | 7/1993 | WIPO . |

OTHER PUBLICATIONS

Chremos, A.N., J. Clin. Gastroenterol., "Clinical Pharmacology of Famotidine: A Summary", vol. 9 (Suppl. 2), pp. 7–12 (1987).

Thompson, et al.,CMA Journal, "Heartburn and globus in apparently healthy people", vol. 126, pp. 46–48 (1982).

Laskin, et al., J. Clin. Pharmacol, "Pharmacodynamics and Dose–Response Relationship of Famotidine: A Double–Blind Randomized Placebo–Controlled Trial", vol. 33, pp. 636–639 (1993).

McCallum et al., Digestive Diseases and Sciences, "MK–208, A Novel Histamine H2–Receptor Inhibitor with Prolonged Antisecretory Effect", vol. 30(12), pp. 1139–1144 (1985).

Gitlin et al., Amer. Journal of Gastroenterology, "A multiclinic Double–Blind Dose Ranging Study Evaluating the Efficacy and . . . ", vol. 80, p. 840 (1985).

Miyoshi et al., Naika Hokan, "Clinical Evaluation of Famotidine on Acute Gastric Mucosal Lesions Associated with Acute Gastritis and . . . ", vol. 34, pp. 442–457 (1987).

Douds, Andrew C. and J. Douglas Maxwell, BMJ,(Letters), vol. 309, p. 1156 (1994).

Cooper, J.R.B., BMJ, (Letters), vol. 309, pp. 1156–1157 (1994).

Simon et al., Esophageal, Gastric, and Duodenal Disorders, "Self–Directed Treatment of Intermittent Heartburn: A Randomized . . . ", p. A181 (1994).

MSD Merck Sharp & Dohme, "PEPCID Insert".

F–D–C Reports—"The Tan Sheet" pp. 9–11, Apr. 18, 1994.

Pepcid AC Acid Control Product Monograph (published 1994).

"The Liberator . . . ", The Pharmaceutical Journal (May 7, 1994.

Database Hcaplus on STN, No. 553610 Over–The–Counter H–2, Medical Letter, 1971.

Database HCA on STN, No. 170225 Pharmaceutical Compositions, WO 9501792, 1995.

Database Hcaplus on STN, No. 142618 Pharmaceutical Compositions, WO 9501795, 1995.

*Primary Examiner*—Thurman K. Page
*Assistant Examiner*—Sharon Howard
*Attorney, Agent, or Firm*—Richard S. Parr; Melvin Winokur

[57] ABSTRACT

A method for preventing heartburn episodes in a patient at risk to development of heartburn, comprising administering to the patient, following the heartburn inducing event but prior to development of heartburn, a composition comprising a pharmaceutically effective amount of an $H_2$ antagonist and an amount of antacid having between about 15 mEq and 46 mEq acid neutralizing capacity.

25 Claims, No Drawings

METHODS AND COMPOSITIONS FOR PREVENTING AND TREATING HEARTBURN

This application claims the benefit of Provisional Appln. Ser. No. 60/027,659 filed Oct. 4, 1996.

BACKGROUND OF THE INVENTION

Heartburn, or pyrosis, is a sensation of pain or burning located substernally or high in the epigastrium with radiation into the neck and occasionally to the arms, associated with regurgitation of acid-peptic gastric juice into the esophagus. Occasional heartburn is common in normal persons, but frequent and severe heartburn is generally a manifestation of esophageal dysfunction. Heartburn may result from abnormal motor activity or distention of the esophagus reflux of acid or bile into the esophagus, or direct esophageal mucosa irritation (esophagitis).

Heartburn is most often associated with gastroesophageal reflux. In this setting, heartburn typically occurs after a meal, with stooping or bending, or when the patient is supine. It may be accompanied by the spontaneous appearance in the mouth of fluid which may be salty, sour, or bitter and green or yellow. Heartburn may arise following the ingestion of certain foods (e.g. citrus fruit juices) or drugs (e.g. alcohol or aspirin).

Reflux esophagitis consists of esophageal mucosal damage resulting from reflux of gastric or intestinal contents into the esophagus. Esophagitis, an inflammation of the esophagus from regurgitation of acid gastric contents, producing substernal pain, develops when the mucosal defenses that normally counteract the effect of injurious agents on the esophageal mucosa succumb to the onslaught of the refluxed acid pepsin or bile. Mild esophagitis shows microscopic changes of mucosal infiltration with granulocytes or eosinophils, hyperplasia of basal cells, and elongation of dermal pegs. Erosive esophagitis shows endoscopically visible damage to the mucosa in the form of marked redness, friability, bleeding, superficial linear ulcers, and exudates.

Known antagonists of the histamine $H_2$ receptor include cimetidine, ranitidine, nizatidine, and famotidine. Famotidine (available from Merck & Co., Inc., Whitehouse Station, N.J., under the name PEPCID®), is 3-{{{2-[(aminoiminomethyl)amino]-4-thiazolyl]methyl]thio]-N-4-(aminosulfonyl)propanimidamide, having the structural formula:

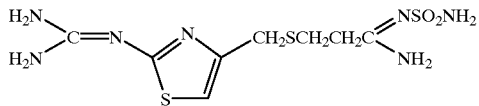

The primary clinically important pharmacologic activity of famotidine is inhibition of gastric secretion. Both acid concentration and volume of gastric secretion are reduced by famotidine. Famotidine is used to treat acid-related disorders such as gastric and duodenal ulcer, gastroesophageal reflux disease and Zollinger Ellison syndrome. Its safety and efficacy have been well established in controlled clinical studies. It is used by over 31 million patients worldwide.

Gitlin et al., *Amer. Journal of Gastroenterology* (1985) vol. 80 pp. 840 examines famotidine efficacy in the treatment of active duodenal ulcers. 20 mg twice daily, 40 mg twice daily and 40 mg at bedtime were administered over a four week period. Healing rates of 67, 75, 70%, respectively, were seen.

Similarly, Miyoshi et al., *Naika Hokan* (1987) vol. 34 pp. 442–457 demonstrates the efficacy of famotidine as a gastritis therapy. Miyoshi et al. evaluated dosage regimens of 5, 10, or 20 mg twice daily in the treatment of gastritis symptom relief. Patients treated with 10 to 20 mg of famotidine had fewer erosions and mucosal haemorrhages than those treated with 5 mg famotidine.

McCallum et al., *Dig. Dis. Sci.* (1985) vol. 30 pp. 1139–1144 describes a study of healthy patients demonstrating that 5 mg of famotidine produces has an effect on gastric acid secretion. Laskin et al., *J. Clin. Pharmacol.* (1993) vol. 33 pp. 636–639 describes a study demonstrating that single doses of 5 and 10 mg of famotidine produces statistically significant decreases in intragastric acidity, beginning at 90–100 minutes and persisting for approximately 9 hours.

Administration of $H_2$ antagonists before ingestion of a heartburn inducing meal may reduce the amount of gastric acid produced and prevent heartburn symptoms. However, $H_2$ antagonists do not neutralize gastric acid, and the onset of the antisecretory effect of $H_2$ antagonists is not instantaneous. Therefore, administration of an $H_2$ antagonist following a meal will not substantially prevent heartburn and related symptoms. Antacids are known to neutralize acid in the stomach and may also act locally in the distal esophagus. Antacids are not known to prevent heartburn when taken before food or beverages which may provoke symptoms.

Wolfe, U.S. Pat. No. 5,229,137, describes compositions and methods which require the simultaneous administration of an $H_2$ antagonist with an antacid to provide relief from pain, discomfort and symptoms associated with episodic heartburn EP 138 540 describes oral compositions containing cimetidine and aluminum hydroxide-magnesium carbonate co-dried gel for treating duodenal, gastric, recurrent and stomal ulceration, and reflux esophagitis. EP 233 853 describes effervescent compositions containing cimetidine and sodium bicarbonate for treating duodenal and gastric ulcers. EP 290 229 describes compositions containing cimetidine, aluminum hydroxide gel, and magnesium hydroxide, for treating duodenal, gastric, recurrent and stomal ulceration, and reflux esophagitis. EP 294 933 describes compositions containing cimetidine, aluminum hydroxide gel and magnesium hydroxide, for treating duodenal, gastric, recurrent and stomal ulceration, and reflux esophagitis. The antacid is described as providing rapid relief from the symptoms of excess stomach acidity by neutralizing acid and the cimetidine is described as bringing about more sustained relief by inhibiting secretion of acid. WO 92/00102 describes coadministration of $H_2$ antagonists with antacids for treating gastric disorders such as hyperacidity. WO 93/12779 describes compositions of $H_2$ antagonists with antacids for treating gastric disorders such as hyperacidity. EP 600 725 describes compositions of famotidine with antacids for treating gastrointestinal distress.

Applicants have now found that administration to a patient of a composition comprising an $H_2$ antagonist and antacid, following a heartburn inducing event such as consumption by the patient of heartburn-inducing food or beverage, but prior to development of heartburn, is an effective means for preventing heartburn or reducing the frequency and severity of postprandial heartburn.

Applicants have also found that compositions comprising about 10 mg famotidine and between about 15 and 46 mEq acid neutralizing capacity of antacid are effective for preventing and treating heartburn symptoms.

SUMMARY OF THE INVENTION

The invention includes a method for preventing heartburn episodes in a patient at risk to development of heartburn, comprising administering to the patient, following the heartburn inducing event but prior to development of heartburn, a composition comprising a pharmaceutically effective amount of an $H_2$ antagonist and an amount of antacid having between about 15 mEq and 46 mEq acid neutralizing capacity (ANC). The invention is also a composition comprising about 10 mg famotidine and an amount of antacid between about 15 mEq and 46 mEq ANC. The invention is also a method for treating heartburn symptoms in a patient which comprises administering to the patient an effective amount of a composition comprising about 10 mg famotidine and an amount of antacid between about 15 mEq and 46 mEq ANC.

DETAILED DESCRIPTION OF THE INVENTION

The invention includes methods for preventing, reducing the frequency and severity of, precluding symptoms associated with, and reducing the risk of heartburn episodes in a patient at risk to development of heartburn, comprising administering to the patient, following the heartburn inducing event but prior to development of heartburn, a composition comprising a pharmaceutically effective amount of an $H_2$ antagonist and an amount of antacid having between about 15 mEq and 46 mEq ANC. These methods are effective for preventing heartburn related symptoms such as acid indigestion and sour stomach.

In one class of methods, the heartburn inducing event is ingestion of a meal which stimulates gastric acid secretion. In a subclass of this class, the $H_2$ antagonist is famotidine. In a group of this subclass, the amount of antacid has between about 21 mEq and 42 ANC. In a subgroup of this group, the amount of antacid has about 21 ANC. In a family of this subgroup, the amount of famotidine is about 10 mg.

The invention also includes a method for treating heartburn symptoms in a patient comprising administering to the patient a pharmaceutically effective amount of a composition comprising about 10 mg famotidine and an amount of antacid having between about 15 mEq and 46 mEq ANC.

The invention also includes compositions comprising about 10 mg famotidine and an amount of antacid having between about 15 mEq and 46 mEq ANC. In a class of these compositions, the amount of antacid has between about 21 mEq and 42 mEq ANC. In a subclass of this class, the amount of antacid has about 21 mEq ANC.

In a particular embodiment of the compositions of the invention, the composition is in the form of a chewable tablet, the amount of famotidine is about 10 mg, and the amount of antacid is about 21 mEq ANC.

The compositions of the invention, when administered following the heartburn inducing event, show a faster onset of relief than $H_2$ antagonists alone, and a longer duration of relief than antacid. The duration of action of the $H_2$ antagonist is at least equal to that of a comparable amount of $H_2$ antagonist administered without antacid.

The term "preventing heartburn episodes" means precluding symptoms, or reducing the severity of symptoms, associated with heartburn in patients susceptible to heartburn following ingestion of heartburn-inducing food or beverage.

The term "precluding symptoms" means making the experience of symptoms impossible or largely ineffectual by removing the conditions needed for them.

The term "reducing the frequency and severity of postprandial heartburn" means substantially lowering the degree of pain associated with heartburn symptoms that would ordinarily occur in patients susceptible to heartburn following ingestion of heartburn-inducing food or beverage.

The term "reducing the risk of heartburn episodes" means substantially lowering the tendency of patients susceptible to heartburn, following ingestion of heartburn-inducing food or beverage, to experience symptoms associated with heartburn following ingestion of heartburn-inducing food or beverage.

The term "heartburn inducing event" includes experience by the patient associated with stimulation of gastric acid secretion and development of heartburn symptoms, such as stress or ingestion of a meal which stimulates gastric acid secretion.

The term "heartburn-inducing food or beverage" includes foods and beverages commonly associated with heartburn in patients susceptible to food- or beverage-induced heartburn episodes, e.g. tomatoes, chili, coffee, red wine, citrus juice, etc. For purposes of describing the invention, the term "meal" is hereinafter to be understood to mean heartburn-inducing food and/or beverage.

The degree of heartburn pain associated with ingestion of such foods varies among individuals and with food types. Thus, some individuals may be more sensitive to certain heartburn-inducing foods than are other individuals. The tendency for a given individual to experience heartburn in response to ingestion of a particular food or beverage is predictable, however, and the individual is able to determine, prior to ingestion, which food or beverage will induce heartburn symptoms.

A "patient susceptible to suffering heartburn episodes following ingestion of heartburn-inducing food or beverage" means any patient who ordinarily experiences symptoms of heartburn caused by ingestion of heartburn-inducing food or beverage.

The antacids suitable for the present invention typically are selected from, but are not limited to, magnesium hydroxide, magnesium carbonate, calcium carbonate and co-dried gels. Calcium and magnesium antacids are preferred antacids.

The $H_2$ antagonists suitable for the methods of the invention for preventing heartburn include, but are not limited to, famotidine, cimetidine, ranitidine, and nizatidine. Preferable, the $H_2$ antagonist is famotidine. Suitable amounts of famotidine are in the range between about 5 mg and 160 mg, preferable between about 5 mg and 80 mg, e.g. 5 mg, 1.0 mg, 20 mg, and 40 mg.

In compositions of the invention, amounts of antacid between about 15 and 4.6 mEq ANC provide immediate preventative and therapeutic relief necessary for effective prevention and treatment of heartburn symptoms. Antacids have known theoretical ANC values (e.g. the ANC of calcium carbonate is 0.020 mEq/mg, and of magnesium hydroxide is 0.0343 mEq/mg—see The United States Pharmacopeia USP 23 NF 18, page 1732 which describes an assay for measuring acid-neutralizing capacity of test substances), and determination of the amount of a specified antacid required to provide a specified ANC can be readily done by persons skilled in the art.

The compositions may also contain pharmaceutically acceptable carriers. Compositions may be formulated for oral administration in solid or liquid form, for example as effervescent or non-effervescent powders or tablets (including chewable and non-chewable tablets), capsules, lozenges, suspensions or dispersions. Compositions may thus be formulated by admixture with pharmaceutically acceptable vehicles additionally containing, as desired, pharmaceutically acceptable adjuvants including thickeners, preservatives, coloring agents, flavoring agents and sweeteners, e.g. aspartame, cyclamate and saccharin.

Powder formulations can be prepared by dry blending ingredients under conditions of controlled temperature and humidity using conventional equipment. Tablet formulations can be prepared by combining the active components with tableting aids, fillers and palatability aids in a conventional manner and tableting on a conventional machine.

The compositions can be in the form of chewable tablets that disintegrate readily in the mouth when chewed. Such tablets can be prepared by technology known in the art, including, for example, methods for preparing tablets with barrier layers, such as those described in European Patent Publication 600 725, hereby incorporated by reference. Such technology is effective for masking the bitter taste associated with $H_2$ antagonists.

In the example shown below, tablets comprising famotidine and antacid, and amounts of inactive ingredients such as binders, e.g. dextrates and pregelatinized starch, flavors, lubricants e.g. magnesium stearate, colorants, e.g. red ferric oxide, sweetener, e.g. confectioner's sugar, granulating excipient, e.g. lactose hydrous and hydroxy methylcellulose, particle coating such as cellulose acetate and hydroxypropyl cellulose, and wetting agents, e.g. sodium lauryl sulfate sufficient to prepare a pharmaceutically acceptable tablet for delivery of the active famotidine and antacid, were prepared.

EXAMPLE 1

A chewable tablet which includes 10 mg famotidine, 800 mg calcium carbonate and 165 mg magnesium hydroxide (which amounts of calcium carbonate and magnesium hydroxide provide 21 mEq ANC) was prepared in the following manner.

An uncoated famotidine rotorgranulation was prepared by dry blending famotidine with various granulating excipients according to the procedure outlined in European Patent Publication 600 725.

A rotorgranulated and coated famotidine granulation intermediate was blended with a directly commpressible grade of calcium carbonate (DESTAB 95S, available from Particle Dynamics) and a directly compressible magnesium hydroxide powder, dextrates, confectioner's sugar granulation, color, flavors, and then blended. Magnesium stearate was then added to the blender to form the final blend. The lubricated mixture was compressed into single-layer, round pale rose colored tablets on appropriate tooling.

The following table lists specific ingredients and amounts which were used to prepare, according to the above process, a pharmaceutical composition comprising famotidine and antacid.

| Ingredient | % Dry | mg/tablet | mg/tablet |
|---|---|---|---|
| Confectioner's Sugar | | | 136.7 |
| Dextrates | | | 500.00 |
| Coated Famotidine Granulation | | | 86.4 |
| Famotidine | 11.57 | 10.00 | |
| Excipients | | 76.4 | |
| Peppermint | | | 11.0 |
| N & A International Creme | | | 2.50 |
| Magnesium Hydroxide Powder DC | | | 168.4 |
| Rose Colorant | | | 27.7 |
| Calcium Carbonate (DESTAB 95S, Particle Dynamics) | | | 842.1 |

-continued

| Ingredient | % Dry | mg/tablet | mg/tablet |
|---|---|---|---|
| Magnesium Stearate | | | 5.15 |
| Total Tablet Weight | | | 1780 mg |

EXAMPLE 2

The procedure of Example 1 is followed, using 330 mg magnesium hydroxide and 1600 mg calcium carbonate, to provide a famotidine/antacid chewable tablet having 42 ANC.

EXAMPLE 3

A non-chewable tablet having the following composition is prepared:

| Ingredient | mg |
|---|---|
| Famotidine | 10.0 |
| Magnesium hydroxide | 165.0 |
| Calcium carbonate | 800.0 |
| Magnesium stearate | 5.0 |
| Pregelatinized starch | 40.0 |
| Carboxymethylcellulose | 100.0 |

Famotidine, magnesium hydroxide, calcium carbonate, carboxymethylcellulose, and a portion of the starch are mixed and granulated. The resulting granulation is sieved, dried and blended with the remainder of the corn starch and the magnesium stearate. The resulting granulation is then compressed into tablets.

EXAMPLE 4

A non-chewable tablet having the following composition is prepared:

| Ingredient | mg |
|---|---|
| Coated famotidine granulation | 86.4 |
| Magnesium hydroxide | 165.0 |
| Calcium carbonate | 800.0 |
| Magnesium stearate | 5.0 |
| Pregelatinized starch | 40.0 |
| Carboxymethylcellulose | 100.0 |

Coated famotidine granulation (used in Example 1), magnesium hydroxide, calcium carbonate, carboxymethylcellulose, and a portion of the starch are mixed and granulated. The resulting granulation is sieved, dried and blended with the remainder of the corn starch and the magnesium stearate. The resulting granulation is then compressed into tablets.

EXAMPLE 5

A non-chewable tablet having the following composition is prepared:

| Ingredient | mg |
|---|---|
| Famotidine | 10.0 |
| Magnesium hydroxide | 330.0 |
| Calcium carbonate | 1600.0 |

-continued

| Ingredient | mg |
|---|---|
| Magnesium stearate | 5.0 |
| Pregelatinized starch | 40.0 |
| Carboxymethylcellulose | 100.0 |

Famotidine, magnesium hydroxide, calcium carbonate, carboxymethylcellulose, and a portion of the starch are mixed and granulated. The resulting granulation is sieved, dried and blended with the remainder of the corn starch and the magnesium stearate. The resulting granulation is then compressed into tablets.

EXAMPLE 6

Adult male and female patients having a history of heartburn, acid indigestion, or sour/upset stomach are given a meal of chili and burgundy wine. Tablets prepared according to Example 1 are administered to the patients after consumption of the meal but prior to development of heartburn symptoms, decreasing the likelihood of heartburn.

EXAMPLE 7

Adult male and female patients having a history of heartburn, acid indigestion, or sour/upset stomach are given a meal of chili and burgundy wine. Tablets prepared according to Example 1 are administered to the patients after development of heartburn symptoms induced by the meal, relieving pain associated with heartburn.

What is claimed is:

1. A method for preventing heartburn episodes in a patient at risk to development of heartburn, comprising administering to the patient, following a heartburn inducing event but prior to development of heartburn, a composition comprising a pharmaceutically effective amount of an $H_2$ antagonist and an amount of antacid having between about 15 mEq and 46 mEq acid neutralizing capacity.

2. A method of claim 1 wherein the heartburn inducing event is ingestion of a meal which stimulates gastric acid secretion.

3. A method of claim 2 wherein the $H_2$ antagonist is famotidine.

4. A method of claim 3 wherein the amount of antacid has between about 21 mEq and 42 mEq acid neutralizing capacity.

5. A method of claim 4 wherein the amount of antacid has about 21 mEq acid neutralizing capacity.

6. A method for reducing the frequency and severity of heartburn episodes in a patient at risk to development of heartburn, comprising administering to the patient, following a heartburn inducing event but prior to development of heartburn, a composition comprising a pharmaceutically effective amount of an $H_2$ antagonist and an amount of antacid having between about 15 mEq and 46 mEq acid neutralizing capacity.

7. A method of claim 6 wherein the heartburn inducing event is ingestion of a meal which stimulates gastric acid secretion.

8. A method of claim 7 wherein the $H_2$ antagonist is famotidine.

9. A method of claim 8 wherein the amount of antacid has between about 21 mEq and 42 mEq acid neutralizing capacity.

10. A method of claim 9 wherein the amount of antacid has about 21 mEq acid neutralizing capacity.

11. A method for precluding symptoms associated with heartburn episodes in a patient at risk to development of heartburn, comprising administering to the patient, following a heartburn inducing event but prior to development of heartburn, a composition comprising a pharmaceutically effective amount of an $H_2$ antagonist and an amount of antacid having between about 15 mEq and 46 mEq acid neutralizing capacity.

12. A method of claim 11 wherein the heartburn inducing event is ingestion of a meal which stimulates gastric acid secretion.

13. A method of claim 12 wherein the $H_2$ antagonist is famotidine.

14. A method of claim 13 wherein the amount of antacid has between about 21 mEq and 42 mEq acid neutralizing capacity.

15. A method of claim 14 wherein the amount of antacid has about 21 mEq acid neutralizing capacity.

16. A method for reducing the risk of heartburn episodes in a patient at risk to development of heartburn, comprising administering to the patient, following a heartburn inducing event but prior to development of heartburn, a composition comprising a pharmaceutically effective amount of an $H_2$ antagonist and an amount of antacid having between about 15 mEq and 46 mEq acid neutralizing capacity.

17. A method of claim 16 wherein the heartburn inducing event is ingestion of a meal which stimulates gastric acid secretion.

18. A method of claim 17 wherein the $H_2$ antagonist is famotidine.

19. A method of claim 18 wherein the amount of antacid has between about 21 mEq and 42 mEq acid neutralizing capacity.

20. A method of claim 19 wherein the amount of antacid has about 21 mEq acid neutralizing capacity.

21. A composition comprising about 10 mg famotidine and an amount of antacid between about 15 mEq and 46 mEq acid neutralizing capacity.

22. A composition of claim 21 wherein the amount of antacid having between about 21 mEq and 42 mEq acid neutralizing capacity.

23. A composition of claim 22 wherein the amount of antacid having about 21 mEq acid neutralizing capacity.

24. A composition of claim 23 wherein the composition is in the form of a chewable tablet.

25. A method for treating heartburn episodes in a patient comprising administering to the patient a pharmaceutically effective amount of a composition of claim 21.

* * * * *